United States Patent [19]

Weeks

[11] Plant 4,738

[45] Jun. 9, 1981

[54] ROSE PLANT

[76] Inventor: O. L. Weeks, 4759 Philadelphia St., Chino, Calif. 91710

[21] Appl. No.: 150,633

[22] Filed: May 16, 1980

[51] Int. Cl.[3] ..... A01H 5/00
[52] U.S. Cl. ..... Plt./20
[58] Field of Search ..... Plt./20–21

*Primary Examiner*—Robert E. Bagwill
*Attorney, Agent, or Firm*—Vincent G. Gioia

[57] ABSTRACT

A new hybrid tea rose variety of brilliant red coloring, and occasional petal blackening which is substantially non-fading and long lasting on the plant and as a cut flower.

1 Drawing Figure

The present invention relates to a new and distinct variety of rose plant of the hybrid tea rose class, which was originated by my crossing as seed parent the rose known as "Mister Lincoln" and the rose known as "Mexicana" as pollen parent.

Among the novel characteristics possessed by this new variety which distinguish it from its parents and all other varieties of which I am aware are vibrant, substantially non-fading, red colored flowers which start as dark, almost black red buds and a vigorous plant with attractive green foliage. Open blooms are especially attractive and remain non-fading or bluing and are long lasting on the plant and when cut. Asexual reproduction by budding of the new variety as performed in San Bernardino County, Calif., shows that the foregoing and other distinguishing characteristics come true to form and are established and transmitted through succeeding propagations.

The new and improved rose variety which I have developed is an unusually fine red hybrid tea rose of substantial petalage and which does not "blue" upon aging.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "46A" is plate 46A of the Royal Horticultural Society Color Chart.

Parentage: Seedling.
*Seed parent.*—"Mister Lincoln".
*Pollen parent.*—"Mexicana".
Class: Hybrid tea.

The following observations are made of specimens grown outdors in San Bernardino County, Calif. during the month of September.

1. FLOWER

Blooming Habit: Continuous.

A. Bud:
- (1) *Size.*—Medium.
- (2) *Form.*—Pointed.

- (3) *Color.*—When sepals first divide — 46A. When petals begin to unfurl — 45A.
- (4) *Sepals.*—Fancy, longer than bud, foliated, some serrations, recurve down.
- (5) *Peduncle.*—Length — medium. Aspect — straight. Strength — erect. Color — reddish green to green 138B.

B. Bloom:
- (1) *Size.*—Average size when fully expanded — about 4 to 5 inches.
- (2) *Borne.*—Primarily singly but also in cluster of 2 or 3.
- (3) *Form.*—Ovoid, high centered, petals roll outward.
- (4) *Petalage.*—Number of petals under normal conditions — about 44 to 48.
- (5) *Color.*—Dark red (46A) buds unfurl to persistent 45A ("guardsman red") vibrant red coloring which remains constant as blooms mature and age. Occasional blackening of outer petals may be seen as well.

C. Petals:
- (1) *Texture.*—Thick.
- (2) *Appearance.*—Velvety to satiny.
- (3) *Form.*—Obovate.
- (4) *Arrangement.*—Regularly arranged.
- (5) *Petaloids in center.*—Many.
- (6) *Persistence.*—Drop off cleanly.
- (7) *Fragrance.*—Slight to none.
- (8) *Lasting quality.*—Very long lasting on plant and as cut flower.

2. REPRODUCTIVE ORGANS

A. Stamens, filaments and anthers:
- (1) *Arrangement.*—Regular, about pistils, tucked in calyx.
- (2) *Color.*—Reddish yellow.

B. Pollen: Color — gold.
C. Styles: Uneven, medium, bunched.
D. Stigmas: Color — yellow.
E. Hips: Nonobserved.

3. PLANT

A. Form: Upright.
B. Growth: Vigorous, free branching.
C. Foliage: Compound 3 to 5 leaflets.
- (1) *Size.*—Medium to large.
- (2) *Quantity.*—Abundant.

(3) *Color.*—New foliage: Purplish becoming green 139C. Old foliage: Upper side — near to 139A. Under side — near to 139C.

(4) *Shape.*—Oval, acute apex.

(5) *Texture.*—Upper side is glossy and under side is dull.

(6) *Edge.*—Serrated.

(7) *Serration.*—Simple.

(8) *Leaf stem.*—Color — near to 138B.

(9) *Stipules.*—Long.

(10) *Resistance to disease.*—Mildew — good. Rust — good.

D. Wood:

(1) *New wood.*—Color — near 138B. Bark — Smooth, shiny.

(2) *Old wood.*—Color — near 138A. Bark — smooth, shiny.

E. Thorns:

(1) *Thorns.*—Quantity (main stalk): ordinary. On laterals from stalk — few. Form — straight, pointed. Length — medium. Color — tan. Position — scattered.

(2) *Prickles.*—Few.

F. Winter hardiness: Good winter hardiness.

I claim:

1. A new and distinct variety of rose plant of the hybrid tea class, substantially as shown and described, characterized particularly by flowers of persistent vibrant red coloring which hold well upon aging and are long lasting on the plant and as cut flowers.

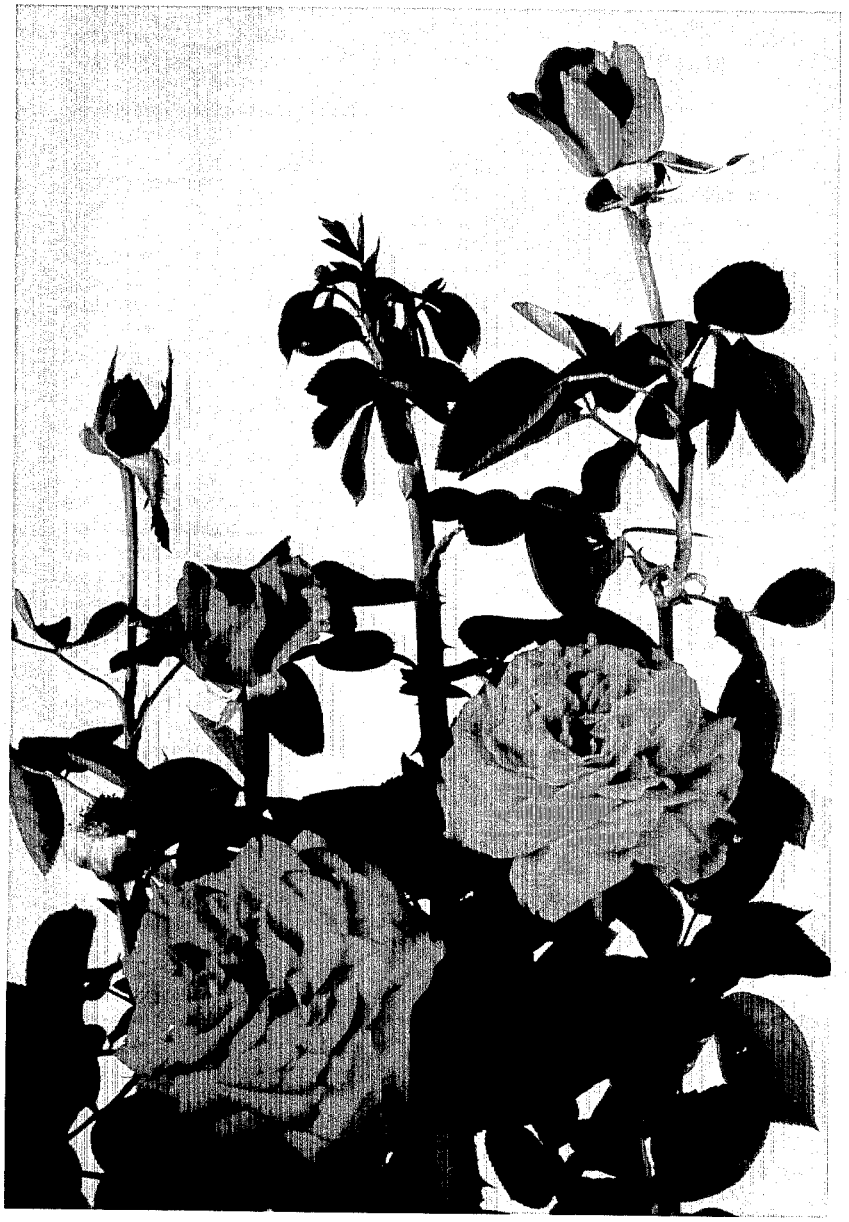

* * * * *